United States Patent [19]

Rothenberg et al.

[11] Patent Number: 4,673,651

[45] Date of Patent: Jun. 16, 1987

[54] MULTI-CELL TRAY

[76] Inventors: Barry E. Rothenberg, 232 Barbara Ave.; James O. Billups, Jr., 143 S. Cedros Ave., both of Solana Beach, Calif. 92075

[21] Appl. No.: 712,413

[22] Filed: Mar. 15, 1985

[51] Int. Cl.⁴ ............................................. C12M 1/20
[52] U.S. Cl. .................................... 435/301; 220/23.8
[58] Field of Search ........................ 435/284, 297–301; 220/21, 23.8; 422/99, 101, 102; 159/16.1

[56] References Cited

U.S. PATENT DOCUMENTS

| | | | |
|---|---|---|---|
| 2,959,870 | 11/1960 | Vandercook | 34/151 |
| 3,591,461 | 7/1971 | Bazil et al. | 195/142 |
| 3,597,326 | 8/1971 | Liner | 435/301 |
| 4,010,078 | 3/1977 | Taylor | 195/139 |
| 4,012,288 | 3/1977 | Lyman et al. | 195/139 |

OTHER PUBLICATIONS

"American Biotechnology Laboratory" Journal, Nov. 1984, advertisement for Becton Dickinson Falcon MicroTest III Culture Plate.

Primary Examiner—Samuel Scott
Assistant Examiner—Noah Kamen
Attorney, Agent, or Firm—Brown, Martin, Haller & Meador

[57] ABSTRACT

A multi-cell tray comprises a base having an upper wall and side walls defining an outer periphery, with a plurality of cells for receiving test media in the upper wall, and a removable cover on the base having side walls depending downwardly from a top wall, with the side walls of the base and cover being spaced apart to define a passageway for gas to enter the tray. A baffle encompasses the cell area of the base and extends upwardly from the upper wall of the base to deflect incoming gas upwardly away from the level of the cells, with passageways uppermost of the baffle for allowing the deflected gas to enter a chamber above the cells defined between the spaced upper walls of the base and cover.

5 Claims, 9 Drawing Figures

MULTI-CELL TRAY

BACKGROUND OF THE INVENTION

The present invention relates to a tray comprising a base in which a plurality of cells are formed and a removable cover or lid for the tray. The cells in the tray may be used to contain various media for testing, experimental, and other purposes. Trays of this type may be used, for example, as culture trays for tissue cultures.

In trays of this type there is normally a clearance between the base and cover to allow air or other gas, e.g., $CO_2$, to circulate to the cells. The clearance is normally provided by raised beads or ribs in the cover or base which hold the two parts in a spaced relationship. This type of tray is shown, for example, in U.S. Pat. Nos. 3,597,326 of Liner and 4,012,288 of Lyman et al. The cover or lid in U.S. Pat. No. 4,012,288 is held spaced from the base by a series of support posts on the base on which it rests. The lid itself has protruding ridges in its inner surface which extend around the edges of the individual cells when the cover is in place to help prevent contamination between the cells as a result of condensation. One problem with such trays is the so-called 'edge effect'. The gas flow pattern is such that the outer and corner cells are exposed to a greater gas flow than the inner cells. When such trays are used as tissue culture trays, the outer trays will evaporate more quickly than that in the inner cells. This gives rise to significant evaporation losses, uneven culture results, and experimental errors. It has been shown that the edge effect is more enhanced at the corner cells than the side edge cells, and can produce evaporation losses of the order of 15% at the side edges and more than 25% at the corner cells. In an effort to avoid such errors some experimentalists in the past have simply left the outermost cells of such trays empty.

SUMMARY OF THE INVENTION

It is an object of the present invention to provide multi-cell tray in which the so-called edge effect is rduced, giving improved accuracy in results when all the cells are used.

According to the present invention a tray is provided which comprises a base having a plurality of cells for containing test media, and a cover or lid arranged to fit over the base so that it is held spaced above the base to define a substantially enclosed plenum chamber above the cells. Restricted passageways are provided for communicating the exterior of the tray with the chamber to allow gas to flow into the chamber in a controlled fashion. The passageways are arranged to disperse the gas flow into the chamber so that it is distributed in a more even fashion to all the cells. This tends to reduce the so-called 'edge effects' of uneven evaporation substantially.

The passageways may be provided in a vertical baffle extending around some or all of the outer periphery of the cell containing area of the base. The baffle may be provided in the lid or in the base, and may additionally comprise the means for spacing the lid above the base. In this case spaced openings or ports are provided in the baffle which comprise the restricted passageways for dispersing gas into the chamber. Alternatively, separate means for spacing the lid above the base may be provided so that a gap is left between the upper edge of the baffle and the lid, the gap comprising a restricted passageway for dispersing gas into the chamber.

In these arrangements the gas does not flow directly over the outer cells as it enters the spacing above the cell, as in the past, but is deflected away from them by the baffle and flows towards and across the cover to be dispersed more gradually to all the cells.

In an alternative arrangement a horizontal baffle plate is mounted in the cover so as to form the upper wall of the chamber above the cells. The plate has a series of openings so that gas flowing into the spacing between the cover and plate is dispersed substantially equally to all the cells. Preferably the plate has openings at locations corresponding to the areas between individual cells, so that gas is not directed downwardly directly into the individual cells. Suitable arrangements are made to circulate gas to the space above the plate so that it is dispersed to the area above the cells via the openings in the plate.

According to another embodiments of the invention the passageways are provided in the base of the tray and gas is circulated upwards through the passageways into the chamber above the cells. In this arrangement the base is provided with a chamber below the cells into which gas can flow, and openings are provided in the cell-containing upper wall of the base between the individual cells to allow gas to flow into the spacing above the cells. Again the openings are arranged such that gas is dispersed substantially equally to all the cells.

Thus the multi-cell tray according to the present invention has the advantage that gas, for example air or $CO_2$, is dispersed more evenly to all the cells to reduce the problems of uneven evaporation losses at the edge or corner cells.

BRIEF DESCRIPTION OF THE DRAWINGS

The above and other advantages of the present invention will be more apparent from the following description together with the drawings, in which like reference numerals refer to like parts throughout, and in which.

DESCRIPTION OF THE PREFERRED EMBODIMENTS

Figure 1:
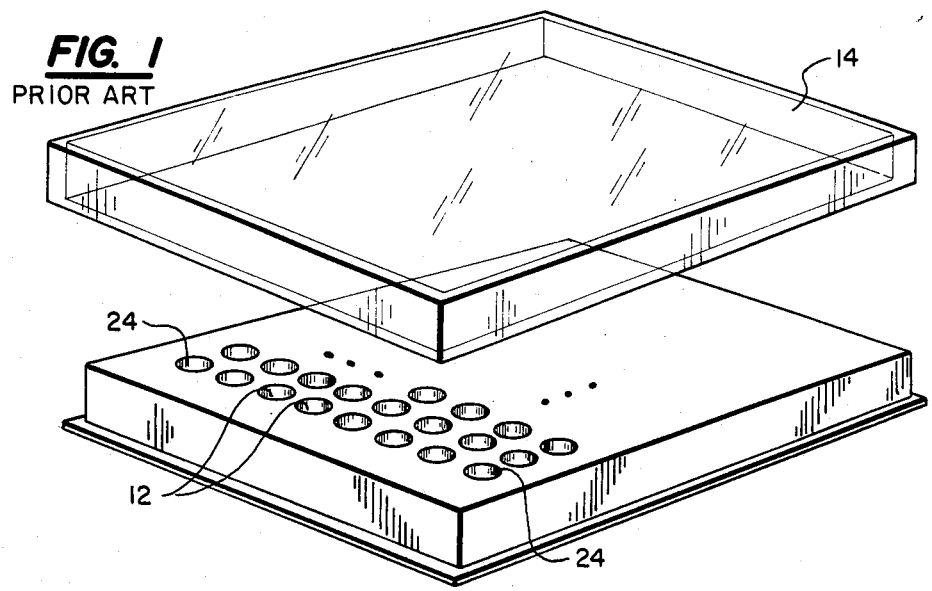
FIG. 1 is a perspective view of the base of a multicell tray having a plurality of cells for containing test media such as tissue cultures for testing or experimental purposes.

FIG. 1 of the drawings shows the base 10 of a multi-cell tray having a number of individual cells 12 in which various media may be placed for testing, experimental, or other purposes. One use for such a tray is as a culture tray in which tissue cultures are placed in the various cells. However, there are clearly many other possible uses for the tray. It may be used in any experimental environment where one or more liquids must be subjected to the same conditions for prolonged periods of time. It will be understood that such trays may be provided with a greater or smaller number of cells than shown in FIG. 1, and that the tray need not be of rectangular shape as shown but may be of circular or other shapes.

Figure 2:
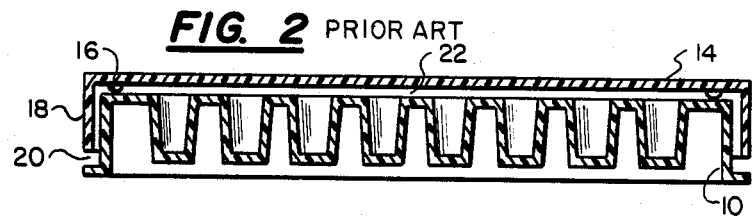
FIG. 2 is a cross-section on the lines 2—2 of FIG. 1 with the cover or lid of the tray in place, showing a prior art arrangement.

In the past such tray bases have been covered by conventional removable covers or lids 14 of the type shown in FIG. 2. The dimensions of the cover 14 are slightly larger than those of the base 10 and ribs or spacers 16 are provided either in the cover 14 or the base 10 in order to hold the cover 14 spaced above the level of the base 10. The gap between the rim 18 of the cover and the tray allows gas such as air to flow in the direction of the arrow 20 in FIG. 2 into the spacing 22 defined between the cover and base of the tray. Thus the cover allows exposure of the material in the cells to a gas such as air while preventing or restricting contamination of the material. One problem with culture trays of this type is that the outermost cells are exposed to a greater air flow than the inner cells, with the result that uneven rates of evaporation occur. This effect is even more noticeable at the corner cells 24, where the material in the cells will evaporate much faster than that in the inner cells. This gives rise to uneven results and often unacceptable experimental errors.

Figure 3:
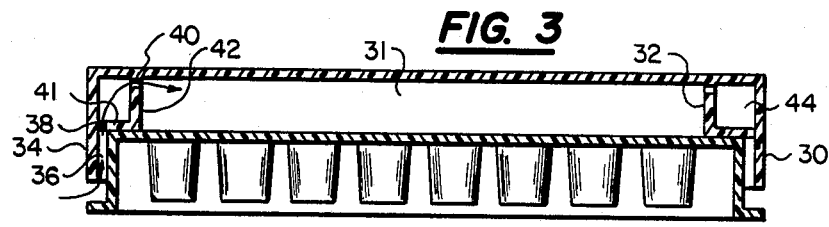
FIG. 3 is a cross-sectional view similar to FIG. 2 showing a multi-cell tray according to a first embodiment of the present invention.
Figure 4:
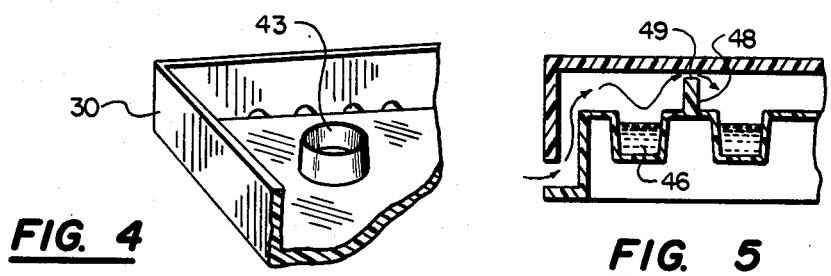
FIG. 4 is a perspective view showing the interior or the lid or cover of FIG. 3.

FIGS. 3 and 4 show a first embodiment of a multi-cell tray according to the present invention. In this embodiment a base 10 of the general type shown in FIG. 1 comprises an upper wall and side walls defining an outer periphery, a plurality of cells being provided within a cell area in the upper wall of the base as shown. A removable cover 30 is placed on the base, the cover having an upper wall and side walls 34 extending downwardly from the upper wall. The side walls of the base and cover are spaced apart to define a first passageway or gap 36 for incoming gas. A vertical baffle extends around the cell area and projects upwardly from the upper wall of the base when the cover is placed on the base as shown in FIG. 3, the baffle, together with the spaced upper walls of the base and cover, defining a plenum chamber 31 above the cells. The baffle has second passageways 40 uppermost of the baffle for allowing gas flowing into the tray via first passageway 36 to enter chamber 31 in the direction of the arrows in FIG. 3. Thus the baffle acts to deflect incoming gas upwardly away from the cell openings. In the embodiment shown in FIG. 3 the baffle 32 is of inverted L-section and is secured around the inner periphery of the cover.

The baffle 32 has a series of passageways or ports 38, 40 about its horizontal and vertical faces 41, 42 respectively, which serve to restrict and disperse gas flow into the plenum chamber 31 defined between the base and the cover. The ports 40 in the vertical section of the baffle communicating with the chamber 31 are arranged to disperse the gas flowing into the chamber so that gas flow over the cells is substantially equal and edge effects are reduced or substantially eliminated. Clearly the L-shaped baffle shown in FIG. 3 may be replaced with a simple vertical baffle between the base and cover, and the raised baffle may be provided around the upper face of the base 10 surrounding the cell area instead of in the cover 30. In another modified embodiment, separate ribs or spacers may be provided to space the cover above the base, with the resultant gap between the upper edge of the baffle and the cover comprising the restricted passageway for dispersing the gas flow into the chamber, in place of the individual openings shown in FIG. 3.

The cover 30 is shown in FIG. 4 with downwardly projecting condensation rings 43 which will register with the individual cells when the cover is placed over the base in order to reduce the risk of condensation contamination between cells. However, the condensation rings are not essential to the present invention and may be eliminated in an alternative embodiment.

Figure 5:
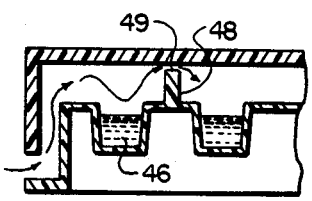
FIG. 5 is a partial cross-sectional view similar to FIG. 3 showing a modification to the embodiment of FIG. 3.

FIG. 5 shows another modification to the embodiment shown in FIG. 3 in which a trough 46 is provided in the base 10 surrounding the cells and an upstanding baffle 48 is positioned between the trough and the cells. The trough may be filled with water, for example, so that gas flowing into the tray in the direction of the arrows in FIG. 5 will be humidified and then dispersed through ports or a gap 49 provided in the baffle into the chamber 49 above the cells.

Although the gas dispersing baffle shown in the above embodiments extends around the entire periphery of the cell area, it may alternatively be provided with gaps in its periphery rather than ports to disperse the gas flow. The baffle acts to deflect gas upwardly away from the cells to flow across the cover, where it disperses downwardly.

Figure 6:
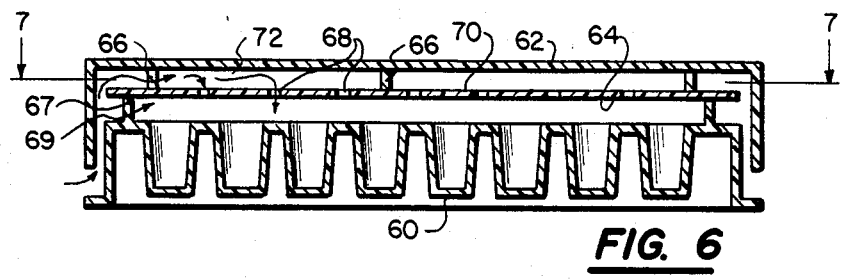
FIG. 6 is a cross-sectional view similar to FIGS. 2 and 3 showing a multi-cell tray according to a second embodiment of the present invention.
Figure 7:
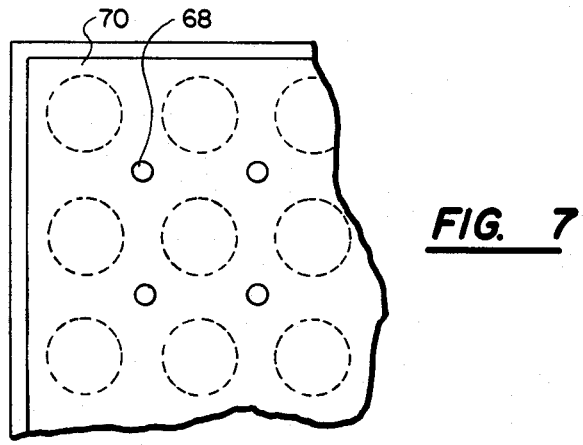
FIG. 7 is a cross-sectional view on the line 7—7 of FIG. 6 showing the cells in phantom to illustrate the relative positioning of the openings in the baffle plate and the cells in the culture tray of FIG. 5.

FIGS. 6 and 7 show a second embodiment of the present invention. In FIG. 6 a tray base 60 of the general type shown in FIG. 1 is provided with a cover 62 which has a horizontal plate 64 spaced below its inner face and secured to it by means of suitable spaced snap fittings or connecting ribs 66. The base 60 has a raised rim or baffle 67 around its periphery which is adapted to engage and form a seal with the undersurface of the plate 64 when the cover is placed over the base as shown in FIG. 6, so as to space the plate 64 above the base to define a chamber 69. The plate 64 has a series of openings or ports 68 across its surface, which are positioned so that when the cover is placed over the base the openings will lie over the gaps between the cells 70 in the base, as shown in FIG. 7.

Thus incoming gas will first enter the tray via the first passageway defined between the spaced side walls of the base and cover, will then be deflected upwardly over the plate 64 via the baffle 67 and through second passageways defined between the ribs 66 above the baffle 67, and will then enter the chamber above the cells via third passageways which comprise the openings 68 in plate 64, which further restrict the gas flow into the cell area. The gas flow is indicated by the arrows in FIG. 7. The openings 68 are preferably positioned such that gas is not directed downwardly directly into a cell. With this arrangement it can be seen that the gas will be dispersed substantially equally to all the cells. If desired condensation rings may be provided in the undersurface of the baffle plate to overlie the individual cells and reduce the risk of contamination between the cells. FIG. 4 shows the provision of condensation rings 43 in a cover or lid, and it will be understood that condensation rings may be provided in the baffle plate 64 in a similar manner.

Figure 8:
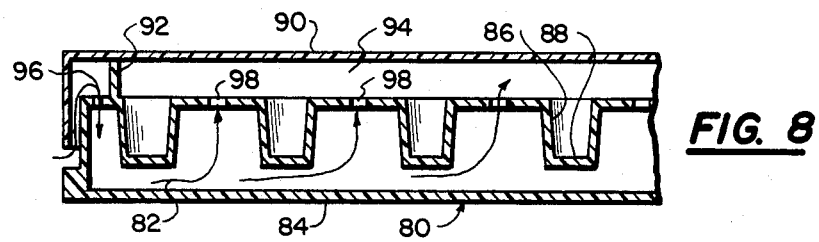
FIG. 8 is a cross-sectional view similar to FIGS. 2 to 5 showing a multi-cell tray according to a third embodiment of the present invention.
Figure 9:
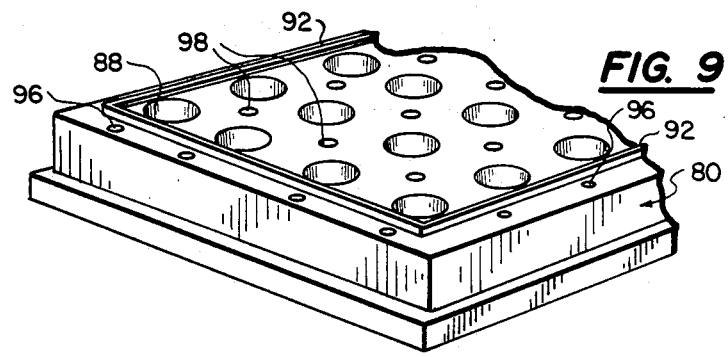
FIG. 9 is a perspective view showing the base of the tray of FIG. 8.

FIGS. 8 and 9 show a third embodiment of the invention in which passageways for dispersing gas into a chamber above the cells are provided in the base of the tray. The base 80 of the tray in this embodiment is modified to include a chamber 82 between a lower wall 84 of the base and the upper wall 86 in which a series of cells 88 are provided in a similar manner to those shown in FIG. 1. A lid or cover 90 is provided which engages with an upstanding ridge 92 around the upper wall of the base 80 when the cover is placed over the base as shown in FIG. 8 so as to leave an enclosed chamber 94 between the upper wall 86 and the cover 90. The cover may be provided with condensation rings (not shown) arranged to register with the individual cells to reduce the risk of condensation contamination, as described above in connection with FIG. 4. An opening or openings 96 around the upper wall of the base outside the ridge 92 allow air to flow in the direction of the arrow into the chamber 82 in the base. The cover and base form a seal against ingress of substantial quantities of gas at their contacting surfaces when the cover is placed over the base.

The upper wall of the base is provided with a series of ports or passageways 98 communicating the chamber 82 in the base with the spacing 94 above the cells. The ports 98 are positioned in the gaps between cells, as best shown in FIG. 9, Gas entering the chamber 82 via opening 96 will be dispersed via ports 98 up through the base of the tray and into the space above the cells, with the ports being arranged such that the gas is dispersed substantially equally to all the cells. If desired a suitable liquid such as water may be provided in the chamber 82 so that air or other gas entering the space above the cells 88 will be humidified. The water will act as a thermal sink surrounding the cells 88 when the chamber is full, thus helping to produce even culture results in all the cells. The multi-cell trays having various gas dispersion arrangements as described above can be provided in various shapes and sizes according to their intended purpose and may be provided with any desired number of cells for containing various test or other material. The trays may be of any suitable material which is non reactive to the materials being tested, but they are preferably of transparent material to allow the user to have a clear and continuous view of the cell contents during testing or experimentation. In a preferred embodiment of invention the trays are molded entirely of plastic material. The trays may be designated so that they can be stacked one on top of the other for storage or to conserve space in an incubator, for example.

While the invention has been described and illustrated above with reference to several preferred embodiments, it will be understood by those skilled in the field that modifications may be made to the disclosed embodiments which are within the scope of the invention as defined by the appended claims.

What is claimed is:

1. A multi-cell tray, comprising:
   a base having an upper wall and side walls defining an outer periphery;
   a plurality of cells in the upper wall of said base within a cell area, the cells having openings at a level for receiving test media;
   a removable cover on said base comprising side walls extending downwardly from an upper wall, the side walls of the base and cover being spaced from one another to define first passageway means;
   baffle means encompassing the cell area and extending upwardly from the upper wall of the base for deflecting incoming gas upwardly away from the level of said cell openings, and having second passageway means uppermost of said baffle means;
   the upper walls of said cover and base and said baffle means together forming a chamber above said cells;
   wherein incoming gas first enters said first passageway means, is then deflected upwardly by said baffle means, and enters into said chamber by said second passageway means, to thereby distribute gas flow substantially evenly around said chamber.

2. The tray according to claim 1, wherein said baffle means comprises a downwardly depending baffle on said cover spaced inwardly of said side walls and positioned to surround the cell containing area of said base, said baffle having a series of ports spaced around its upper periphery comprising said second passageway means.

3. The tray according to claim 1, wherein said baffle means comprises an upwardly projecting baffle integral with said base extending around the cell area of said base.

4. The tray according to claim 1, wherein said baffle means comprises an upwardly projecting baffle on said base, and a transverse plate resting on the upper edge of said baffle and spaced below the upper wall of said cover to define said second passageway means, the transverse plate having a series of spaced openings comprising third passageway means arranged to disperse gas downwardly into said chamber.

5. The tray as in claim 4, wherein said spaced openings are not positioned directly over said cell openings.

* * * * *